US008188143B2

(12) United States Patent
Rao et al.

(10) Patent No.: US 8,188,143 B2
(45) Date of Patent: May 29, 2012

(54) PHARMACEUTICAL COMPOSITION USEFUL AS ACETYLCHOLINESTERASE INHIBITORS

(75) Inventors: Janaswamy Madhusudana Rao, Hyderabad (IN); Bhimapaka China Raju, Hyderabad (IN); Pullela Venkata Srinivas, Hyderabad (IN); Katragadda Suresh Babu, Hyderabad (IN); Jhillu Singh Yadav, Hyderabad (IN); Kondapuram Vijaya Raghvan, Hyderabad (IN); Hemant Kumar Singh, Lucknow (IN); Chandiswar Nath, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/688,359

(22) Filed: Mar. 20, 2007

(65) Prior Publication Data
US 2008/0009544 A1    Jan. 10, 2008

(30) Foreign Application Priority Data
Mar. 20, 2006    (IN) .............................. 735/DEL/2006

(51) Int. Cl.
*A61K 31/35* (2006.01)
(52) U.S. Cl. ...................................................... 514/457
(58) Field of Classification Search ........................ None
See application file for complete search history.

(56) References Cited

U.S. PATENT DOCUMENTS
5,504,088 A    4/1996 Sugimoto et al.
2002/0151560 A1    10/2002 Jacobs et al.
2004/0014648 A1*    1/2004 Neuville .......................... 514/11

FOREIGN PATENT DOCUMENTS
KR    10-0413963    *    6/2002

OTHER PUBLICATIONS

Citation from Chemical Abstracts, 152771u, vol. 91, (1979), p. 196.
Citation from Chemical Abstracts, 268242j, vol. 128, No. 22, (1998).
Citation from Chemical Abstracts, 104326t, vol. 127, No. 8, (1997), p. 71.
Citation from Chemical Abstracts, 1835, vol. 56."Antibiotic properties of some natural coumarins".
Gunatikala, et al. (1994), Journal of Natural Products, "Biological Activity of Some Coumarins from Sri Lankan Rutaceae", vol. 57, No. 4, pp. 518-520.
Elgamal, et al., (1993), Photochemistry, "Coumarins and Coumarin Glucosides from the Fruits of Ammi Majus", vol. 34, No. 3, pp. 819-823.
Luthria, et al., (1989), J. Agric. Food Chem., "Insect Antifeedants from Atalantia racemosa", vol. 37, pp. 1435-1437.
Piazzi, et al., (2003), J. Med. Chem., "3-(4-{[Benzyl(methyl)Amino]methyl)-Phenyl)-6,7-dimethoxy-2H-2-chromenone (Ap2238) Inhibits Both Acetylcholinesterase and Acetylcholinesterase-Induced β-Amyloid Aggregation: A Dual Function Lead for Alzheimer's Disease Therapy", vol. 46, pp. 2279-2282.
Leonetti, et al., (2004), ARKAT USA, Inc. ISSN 1424-376, "Synthesis of potential dual binding site acetylcholinesterase inhibitors through an efficient solid phase approach based on the Mitsunobu reaction", pp. 272-285.
Afek, et al., (1995) Phytochemistry, "Columbianetin, a Phytoalexin associated with Celery Resistance to Pathogens During Storage", vol. 39, No. 6, pp. 1347-1350.
Carmela Gnerre et al.: "Inhibition of Monoamine Oxidases by Functionalized Coumarin Derivatives: Biological Activities, QSARs, and 3D-QSARs," Journal Medicinal Chemistry, 2000, vol. 43, No. 25, pp. 4747-4758.
Corinne Bruhlmann et al.: "Coumarins Derivatives as Dual Inhibitors of Acetylcholinesterase and Monoamine Oxidase," Journal Medicinal Chemistry, 2001, vol. 44, No. 19, pp. 3195-3198.
Katsunoir Tanaka et al.: "Absolute stereochemistry of dihydrofuroangelicins bearing C-8 substituted double bonds: a combined chemical/excition chirality protocol," Org. Biomol. Chem., 2004, vol. 2, No. 1, pp. 48-58.
So Young Kang et al.: "Coumarins Isolated from Angelica gigas Inhibit Acetylcholinesterase: Structure—Activity Relationships," Journal of Natural Products, 2001, vol. 64, No. 5, pp. 683-685.
Miller, et al., "Correlation of in vitro susceptibility with in vivo efficacy in mice for cefoxitin in comparison with cephalosporins", *Journal of Antimicrobial Chemotherapy*, vol. 5, pp. 569-579, (1979).
Sonneveld, et al., "Comparison of In Vitro and In Vivo Screening Models for Androgenic and Estrogenic Activities", *Toxicological Sciences*, vol. 89, No. 1, pp. 173-187, (2006).
Friedlander, "Apoptosis and Caspases in Neurodegenerative Diseases", *New England Journal of Medicine*, vol. 348, pp. 1365-75, (2003).

* cited by examiner

*Primary Examiner* — James D Anderson
*Assistant Examiner* — Gregg Polansky
(74) *Attorney, Agent, or Firm* — McDonnell Boehnen Hulbert & Berghoff LLP

(57) ABSTRACT

The present invention relates to pharmaceutical composition comprising the naturally occurring compounds selected from (±) Marmesin, Columbianetin, Dihydroxanthyletin and substituted coumarin derivatives of 7-allyloxy coumarin, 7-benzyloxy coumarin, 7-methoxy coumarin, 7-acetyloxy coumarin, 4-methyl-7-hydroxy coumarin and 4-methyl-7-acetyloxy coumarin. The said compositions posses a high degree of acetylcholinesterase inhibitory (AChE) property.

1 Claim, 1 Drawing Sheet

PHARMACEUTICAL COMPOSITION USEFUL AS ACETYLCHOLINESTERASE INHIBITORS

FIELD OF THE INVENTION

The present invention relates to a pharmaceutical composition useful as acetylcholinesterase inhibitor (AChE). The present invention particularly relates to the use of natural compounds selected from (±) Marmesin, Columbianetin, Dihydroxanthyletin and substituted coumarin derivatives for the preparation of composition useful as acetylcholinesterase inhibitors.

BACKGROUND OF THE INVENTION

Alzheimer's disease (AD) (J. Med. Chem. 46, 2279, 2003) is a chronic neuro degenerative disorder, which finds severe behavioral abnormalities and loss of cognitive ability. Alzheimer's disease is associated with cerebral cholinergic hypo function and characterized by plaques of the amyloid β-peptide, neurofibrillary tangles and degeneration or atrophy of the basal forebrain cholinergic neurons. The loss of forebrain cholinergic cells results reduction in acetylcholine, which plays an important role in the cognitive impairment associated with Alzheimer's disease. One of the most promising approaches for the treatment of Alzheimer's disease is to increase in the levels of acetyl choline by inhibition of acetycholinesterase.

Several approaches have been developed for the treatment of Alzheimer's disease by inhibiting the AChE. The most used AChE inhibitors are Galanthamine, donepezil, rivastigmine, tacrine and 2H-3,4-tetrahydroquinazoline-2-one & 2H-3,4-tetrahydro quinazoline-2,4-dione (U.S. Pat. No. 5,504,088, 1996) were also reported.

Pyrano coumarins, furo coumarins and substituted coumarins are natural compounds possessing biological activities like purgative (J. Indian. Chem. Soc. Vol 66, 66, 1989), insecticidal (Jpn. Appl. 7 973 12, 1977; Chem. Abstr Vol 91, p 152771u, 1977), antimicrobial (Chem. Abstr. Vol 56, 1835b, 1962), anti feedant (J. Agric. Food. Chem. Vol 37, 1435, 1989), antiulcer (Fitoterapia Vol 68, 410, 1997; Chem. Abstr Vol 128, 268242j, 1998), anti cancer (J. Nat. Prod. Vol 57, 518, 1994) and anti HIV (U.S. Pat. No. 5,637,589; Chem. Abstr. Vol 127, 104326t, 1997). Coumarin derivatives were also exhibited monoamine oxidase (MAO-A& B) inhibitory properties (J. Med. Chem 43, 4747, 2000, J. Med. Chem 44, 3195, 2001, Arkivoc, 272, 2004).

The present invention relates to the compounds of natural sources (±) Marmesin, Columbianetin (Phytochemistry, Vol 39(6), 1347, 1995) Dihydroxanthyletin (Phytochemistry, Vol 34(3), 819, 1993), coumarin derivatives of 7-allyloxy coumarin, 7-benzyloxy coumarin, 7-methoxy coumarin, 7-acetyloxy coumarin, 4-methyl-7-hydroxy coumarin and 4-methyl-7-acetyloxy coumarin are potent highly selective towards the AChE in vitro and in vivo. These compounds are highly effective for the treatment and prevention of AChE.

OBJECTIVE OF THE INVENTION

Figure 1A:
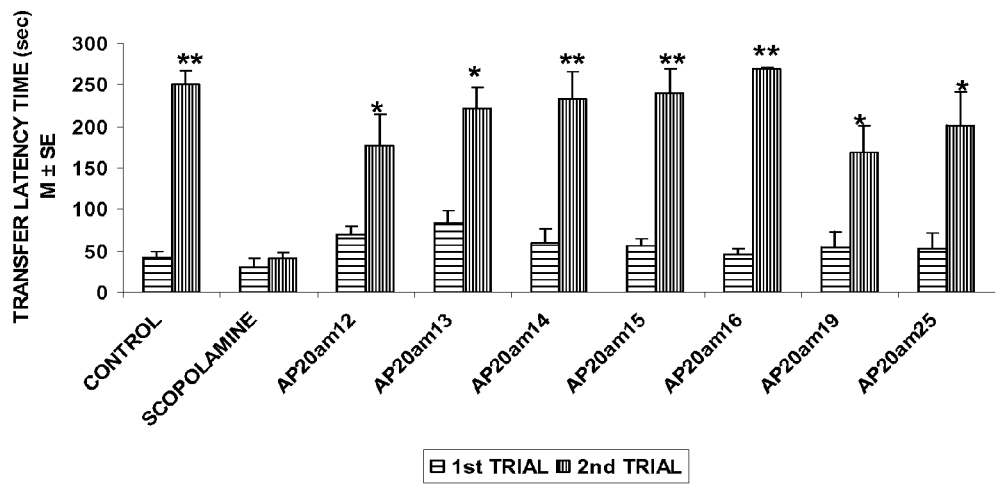
FIG. 1a: Effect of AP 20am Samples (100 mg/Kg, Po×3 Days) on Scopolamine induced Deficit in Passive Avoidance Test in Mice (p**<0.001, *<0.01 Significant difference from 1st Trial, p value determined by student's t Paired test).

The main objective of the present invention is to provide a pharmaceutical composition useful as acetylcholinesterase inhibitor.

Another object of the present invention is to provide the composition wherein the composition exhibit more percent memory retention than standard drug Donepezil, in scopolamine induced memory deficit mice.

One of the objectives of the present invention is to use the naturally occurring compounds for the preparation of (±) Marmesin and Columbianetin.

It is another objective of the present invention is to provide composition using dihydroxanthyletin, useful as AChE inhibitor.

It is further objective of the present invention is to provide composition using compounds 7-allyloxy coumarin, 7-benzyloxy coumarin and 4-methyl-7-acetyloxy coumarins, useful as AChE inhibitor.

It is yet further objective of the present invention is to provide composition using compounds selected from 7-methoxy coumarin, 7-acetyloxy coumarin and 4-methyl-7-hydroxy coumarins, useful as AChE inhibitor.

SUMMARY OF THE INVENTION

Accordingly the present invention provides a pharmaceutical composition comprising an effective amount of compound of formula 1, analogs and pharmaceutically acceptable salts thereof;

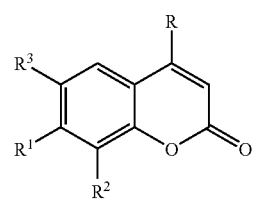

General formula 1

(i) wherein R1 and R2 is linked with each other via the following moiety and collectively makes fused system, R is H, methyl or alkyl, and R3 is H;

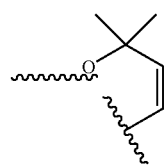

(ii) wherein R1 and R3 is linked with each other via following moiety and collectively makes fused system, R is H, methyl or alkyl, and R2 is H;

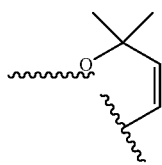

(iii) wherein R1 and R2 is linked with each other via following moiety and collectively makes fused system, R is H, methyl or alkyl, and R3 is H;

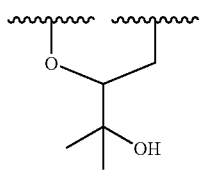

(vi) wherein the value of R, R1, R2, and R3 is selected from the group consisting of 1. $R=R^2=R^3=H; R^1=OH$.
2. $R=R^2=R^3=H; R^1=Prenyl$
3. $R=R^2=R^3=H; R=Allyl$
4. $R=R^2=R^3=H; R^1=2,2$-dimethyl alkyne
5. $R=R^2=R^3=H; R^1=2,2$-dimethyl alkene
6. $R=R^2=R^3=H; R^1=Benzyl$
7. $R=R^2=R^3=H; R^1=Acetyl$
8. $R=R^2=R^3=H; R^1=Methyl$
9. $R=R^1=R^3=H; R^2=Prenyl$
10. $R=R^3=H; R^1=R^2=Prenyl$
11. $R=R^1=R^2=H; R^3=Prenyl$
12. $R=Methyl; R^1=R^2=R^3=H$
13. $R=R^1=Methyl; R^2=R^3=H$
14. $R=R^1=Acetyl; R^2=R^3=H$
15. $R=Methyl; R^1=R^3=H; R^2=OH$
16. $R=Methyl; R^1=Benzyl, R^2=Benzyloxy, R^3=H$
17. $R=Methyl; R^1=Methyl, R^2=Methyloxy, R^3=H$
18. $R=Methyl; R^1=Acetyl, R^2=Acetyloxy, R^3=H$ optionally along with the pharmaceutically acceptable carrier, or diluent, wherein the effective dose of composition is ranging between 50 to 100 mg/kg body weight.

In an embodiment of the present invention, wherein the compound of general formula 1 further comprising:

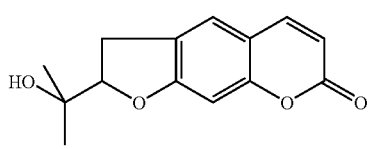

± Marmesin

In an embodiment of the invention, wherein the compound of general formula 1 further comprising:

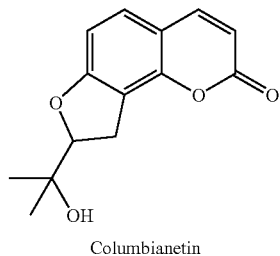

Columbianetin

In another embodiment of the invention, wherein the compound of general formula 1 further comprising:

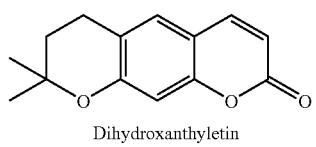

Dihydroxanthyletin

In yet another embodiment of the invention, wherein the compound of general formula 1 further comprising:

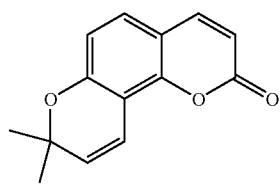

Seselin

In a further embodiment of the invention, wherein the compound of general formula 1 further comprising:

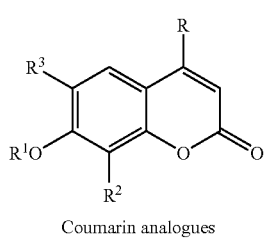

Coumarin analogues

Wherein $R=R^2=R^3\nabla H; R^1=OH$.
$R=R^2=R^3=H; R^1=Prenyl$
$R=R^2=R^3=H; R^1=Allyl$
$R=R^2=R^3=H; R^1=2,2$-dimethyl alkyne
$R=R^2=R^3=H; R^1=2,2$-dimethyl alkene
$R=R^2=R^3=H; R^1=Benzyl$
$R=R^2=R^3=H; R^1=Acetyl$
$R=R^2=R^3=H; R^1=Methyl$
$R=R^1=R^3=H; R^2=Prenyl$
$R=R^3=H; R^1=R^2=Prenyl$
$R=R^1=R^2=H; R^3=Prenyl$
$R=Methyl; R^1=R^2=R^3=H$
$R=R^1=Methyl; R^2=R^3=H$
$R=R^1=Acetyl; R^2=R^3=H$
$R=Methyl; R^1=R^3=H; R^2=OH$
$R=Methyl; R^1=Benzyl, R^2=Benzyloxy, R^3=H$ R=Methyl; R¹=Methyl, R²=Methyloxy, R³=H
R=Methyl; R¹=Acetyl, R²=Acetyloxy, R³=H In yet another embodiment of the invention, wherein the compound used for the preparation of composition is selected from the group consisting of (±) Marmesin, Columbianetin, dihydroxanthyletin, 7-methoxy coumarin, 7-acetyloxy coumarin, 4-methyl-7-hydroxy coumarin, 7-Allyloxycoumarin, and 7-Benzyloxycoumarin.

In an embodiment of the invention, wherein the compounds used for the preparation of composition may be from natural source or synthesized.

In still another embodiment of the invention wherein the composition is useful as acetyl cholinesterase inhibitor.

In a further embodiment of the invention wherein the composition inhibits cholinesterase up to 49%

In still another embodiment of the invention wherein the composition is administered by oral route.

Accordingly the present invention provides a method of treating Alzheimer's disease and related chronic neuron degenerative disorders comprising administering the composition in a subject need thereof wherein the composition comprising an effective amount of compound of formula 1, analogs and pharmaceutically acceptable salts thereof optionally along with the pharmaceutically acceptable carrier, or diluents.

In an embodiment of the invention, wherein the composition is administered by oral route.

In another embodiment of the invention, wherein the composition exhibit more percent memory retention than standard drug Donepezil, in scopolamine induced memory deficit mice.

In a still another embodiment of the invention, wherein the composition comprising the compound selected from group consisting of (±) Marmesin, Columbianetin, Dihydroxanthyletin, 7-Hydroxy-6-prenylcoumarin, 7-Methoxycoumarin, 7-Acetyloxycoumarin, 4-Methyl-7-hydroxycoumarin, 4-Methyl-7-methoxycoumarin, 4-Methyl-7-acetyloxy coumarin, 4-Methyl-7,8-dihydroxycoumarin, 4-Methyl-7,8-dibenzyloxycoumarin, 4-Methyl-7,8-dimethoxycoumarin, and 4-Methyl-7,8-diacetyloxycoumarin inhibiting the AChE in vitro.

In an embodiment of the invention, wherein the composition comprising the compound selected from the group consisting of 7-allyloxy coumarin, 7-benzyloxy coumarin, 7-Methoxycoumarin, 7-Acetyloxycoumarin, 4-Methyl-7-hydroxycoumarin, and 4-methyl-7-acetyloxy coumarins, is inhibiting acetylcholinesterase in vivo

DETAILED DESCRIPTION OF THE INVENTION

The invention is further described in the following examples that are given by the way of illustration and therefore should not be construed to limit the present invention in any manner.

Example-1

Preparation of (±) Marmesin, Columbianetin, Dihydroxanthyletin, Seselin and Coumarin Derivatives The synthetic (±) Marmesin and columbianetin were prepared starting from 7-Hydroxy coumarin (Umbelliferone). Condensation of 7-hydroxy coumarin with 2-chloro-2-methyl but-3-yne in the presence of base gave propargylether. The obtained ether on catalytic hydrogenation afforded alkene. The alkene on claisen rearrangement gave two isomeric products. Oxidation of 7-Hydroxy-6-Prenyl coumarin with m-chloroperbenzoic acid in ethyl acetate solvent gave (±) Marmesin. Oxidation of 7-Hydroxy-8-Prenyl coumarin with m-chloroperbenzoic acid in ethyl acetate solvent gave columbianetin. 7-Hydroxy-6-Prenyl coumarin on oxidation with m-chloroperbenzoic acid in chloroform solvent gave dihydroxanthyletin. (Tetrahedron, 27, 1247, 1971, Tetrahedron, 27, 4901, 1971).

The synthetic seselin was prepared starting from 7-Hydroxy coumarin (Umbelliferone). Condensation of 7-hydroxy coumarin with 2-chloro-2-methyl but-3-yne in the presence of base gave propargylether. The propargylether on heating at 200° C. with N,N-dimethyl aniline gave seselin. (Tetrahedron, 27, 1247, 1971, Tetrahedron, 27, 4901, 1971).

Example-2

Experimental Procedures for In vitro and In vivo Evaluation of (±) Marmesin, Columbianetin, Dihydroxanthyletin, Seselin and Coumarin Derivatives Acetylcholinesterase Inhibiting Potency:

Single trial passive avoidance is widely used as experimental test to assess learning memory functions in rodents. Scopolamine induced impairment in passive avoidance (in vivo) and inhibition of acetylcholinesterase (in vitro) in rodents are commonly employed and screening test to predict potential of an acetylcholinesterase inhibitor as cognitive enhancer (anti-dementic) drug.

Passive Avoidance Test (In Vivo):

The study was conducted in adult Swiss male mice of 3-4 months (wt. 20-25 g) were kept in standard housing condition with 12 h light and dark cycle. The food and water were available ad libitum.

The mice were subjected to single trial passive avoidance test as described by Brioni.

The passive avoidance test was studied by a computerized shuttle box (Columbus Instruments, Ohio, USA) provided with a software program PACS 30. The shuttle box is comprised of two compartments. An automated door was used to isolate the compartments. After an exploration period of 30 s for acclimatization the animal was subjected to a trial of 270 seconds. Each mouse was placed in the bright compartment and on transfer into the dark compartment it was given an electric shock (0.5 mA for 5 s) through floor grid. The transfer of mice from the bright to dark compartment was recorded as transfer latency time (TLT) in seconds. TLT was recorded in control and treated groups ($1^{st}$ Trial, acquisition) and then after 24 h ($2^{nd}$ Trial, retention). An increase in the TLT on $2^{nd}$ Trial (retention) as compared to $1^{st}$ Trial (acquisition) was taken as the criterion for successful learning and memory (cognitive activity).

Scopolamine Induced Deficit (Dementia)

Scopolamine, a muscarinic antagonist known to produce impairment in cognitive functions (dementia) in human as well as in experimental animals, was used to produce deficit (no significant increase on $2^{nd}$ trial) in passive avoidance learning. Scopolamine was administered 5 min prior to $1^{st}$ trial. Reversal of scopolamine induced deficit i.e. significant increase in $2^{nd}$ trial by test substance indicates potential anti-dementia activity. Scopolamine was administered 5 min prior to $1^{st}$ trial.

Drug Administration

The test substance Columbianetin was administered orally in dose of 100 m/kg (1% aqueous suspension in gum acacia) for 3 days. The treated animals were subjected to $1^{st}$ trial after 60 min of 3$^{rd}$ dose of test substance. Scopolamine was administered 5 min prior to 1$^{st}$ trial in test group.

The control group received 1 ml/kg of vehicle (1% aqueous suspension in gum acacia) orally for 3 days. Among the control mice half (n=5) received scopolamine 5 min prior to 1$^{st}$ trial (Control—dementia) and the remaining half were subjected to passive avoidance test (Control—trained).

Figure 1B:
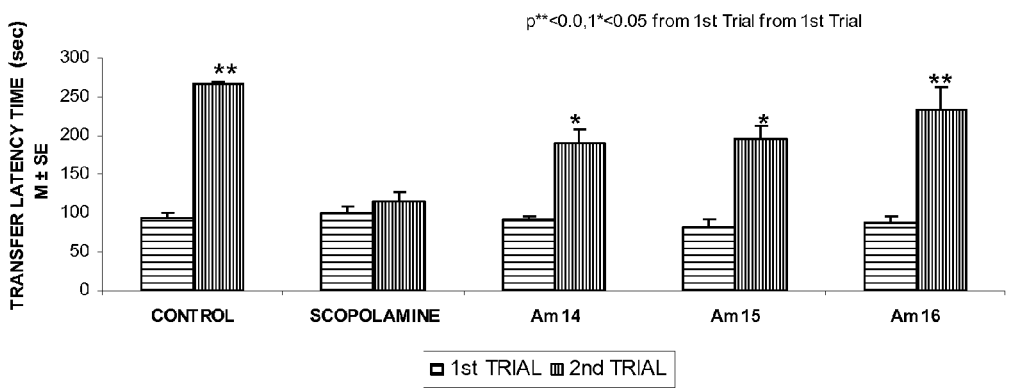
FIG. 1b: Effect of Ap 20am14, 15 & 16 Samples (50 mg/Kg, po×3 Days) on Scopolamine induced Deficit in Passive Avoidance Test in Mice (p**<0.001, *<0.01 Significant difference from 1st Trial, p value determined by student's t Paired test).

The control group showed significant increase in TLT on 2$^{nd}$ trial as compared to 1$^{st}$ trial indicating the successful learning and memory function. Mice treated with scopolamine did not show significant increase in TLT on 2$^{nd}$ trial as compared to 1$^{st}$ trial indicating the deficit in learning and memory function. In the animals pretreated with 7-Allyloxycoumarin (AP20am12), 7-Benzyloxycoumarin (AP20am13), 7-Methoxycoumarin (AP20am14), 7-Acetyloxycoumarin (AP20am15), 4-Methyl-7-hydroxycoumarin (AP20am16) and 4-Methyl-7-acetyloxycoumarin (AP20am19) treatment with scopolamine failed to cause memory deficit as indicated by significant increase in TLT on 2$^{nd}$ trial as compared to 1$^{st}$ trial. See FIGS. 1a and 1b.

Table 1 shows the comparison between of AP20am samples 14, 15 and 16 (50 mg/kg, po) and Standard Drug Donepezil (10 mg/kg, po) on scopolamine induced memory deficit in passive avoidance test on basis of memory retention i.e. % increase in TLT of 2$^{nd}$ trial from TLT of 1$^{st}$ trial. The passive avoidance test is for testing learning and memory functions. Scopolamine is used to produce memory deficit in this test. Inhibition of scopolamine induced memory deficit by a test substance indicate potential of that test sample as memory enhancer. Among these compounds 7-Methoxycoumarin, 7-Acetyloxycoumarin, and 4-Methyl-7-hydroxycoumarin were most effective. The prevention of scopolamine induced memory deficit suggests that 7-Methoxycoumarin, 7-Acetyloxycoumarin, and 4-Methyl-7-hydroxycoumarin have potential for anti-dementia activity.

Level of p value<0.05 indicates statistically significant difference. Lowering in the p value means more significant difference suggesting very significant increase in from TLT from 1$^{st}$ trial.

TABLE 1 comparison data of coumarin compounds with Standard Drug Donepezil

| Groups | % Memory retention |
|---|---|
| Control trained (No scopolamine) | 483 |
| Scopolamine (Memory deficit) | 33 |
| Donepezil + Scopolamine | 288 |
| AP20am 14 + Scopolamine | 295 |
| AP20am 15 + Scopolamine | 321 |
| AP20am 16 + Scopolamine | 376 |

Acetylcholinesterase (AChE) Assay in Brain (In Vitro)

The study was conducted in adult SD male rats (200-250 g). The rats were perfused under mild ether anesthesia through heart with ice cooled normal saline (0.9% NaCl) to reduce blood-borne cholinesterase from the brain. After perfusion the whole brain was taken out. A 10% (w/v) homogenate of brain was prepared first by homogenizing in an Ultra-Turrax T25 homogenizer at a speed of 9500 rpm thrice giving intervals for few seconds in between the runs, with sodium phosphate buffer (30 mmol/lit, pH 7.0). Sodium phosphate buffer was taken in a volume half to the final volume required for 10% homogenate.

1% Triton X-100 (1% w/v in 30 mmol/lit. sodium phosphate buffer, pH 7.0) is then added in a volume to make the final volume for 10% homogenate, slowly while stirring the homogenate on ice. The homogenate was centrifuged at 100,000×g at 4° C. in a Beckman Ultracentrifuge (LE 80) using a fixed angle rotor (80 Ti) for 60 min. Supernatant was collected and stored at 4° C. Aliquots of this supernatant was diluted in the ratio of 1:10 and used as a source of enzyme for the assay.

Enzyme Assay

The assay of AChE was performed according to method described by Ellman et al. A kinetic profile of the enzyme activity was studied spectrophotometrically at 412 nm at an interval of 15 s. The assay for each sample was run in duplicate and each experiment was performed thrice. The specific activity of AChE is expressed in μmoles/min/mg of protein. The test substance (dissolved in DMSO) was incubated with enzyme source in concentration of 100 μg/1 ml of reaction mixture for 30 min at 37° C. prior to obtain kinetic profile of AChE activity. The AChE inhibitory activity was calculated on the basis of % decrease change from control values.

Protein Assay

Protein was estimated in the brain samples by modified Lowry's method. Bovine serum albumin (BSA) was used as standard in the concentration of 1 mg/ml. was estimated in the range of 0.01-0.1 mg/ml.

Results

The results are reported in Table 2. The compounds that showed in vitro inhibition of AChE (25-49%) are (±) Marmesin, Dihydroxanthyletin, 7-Acetyloxycoumarin and 4-Methyl-7-methoxycoumarin. The compounds showed in vitro inhibition of AChE inhibition (20-25%) are 7-Methoxycoumarin, 4-Methyl-7-acetyloxycoumarin, 4-Methyl-7,8-dibenzyloxycoumarin and 4-Methyl-7,8-diacetyloxycoumarin. However, in passive avoidance test (in vivo) 7-Acetyloxycoumarin and 4-Methyl-7-methoxycoumarin were effective. The ineffectiveness of other in vitro active compounds in in vivo passive avoidance test may be due to pharmacokinetics factors like absorption and metabolism.

Statistical Analysis

Mean values and standard error (S.E.) of mean were calculated for TLT and specific activity of AChE in the different regions of brain samples of each group. The significance of difference between the values of AChE activity and TLT of two groups was determined by one-way ANOVA test that followed by Dunnett's test.

TABLE 2

In Vitro and In Vivo data of the coumarin compounds

| Compound | In Vitro %) | In Vivo |
|---|---|---|
| (±) Marmesin | 23.91 | Significant activity (P < 0.01) |
| Columbianetin | 13.93 | No significant activity |
| Dihydroxanthyletin | 37.8 | No significant activity |
| Seselin | | No significant activity |
| 7-Hydroxycoumarin | | No significant activity |
| 7-Prenyloxycoumarin | | No significant activity |
| 7-Hydroxy-6-prenylcoumarin | 42.2 | No significant activity |
| 7-Dimethylpropargylcoumarin | | No significant activity |
| 7-Dimethylalkenylcoumarin | | No significant activity |
| 7-Hydroxy-8-prenylcoumarin | | No significant activity |
| 7-Allyloxycoumarin | | Significant activity (P < 0.05) |
| 7-Benzyloxycoumarin | | Significant activity (P < 0.005) |
| 7-Methoxycoumarin | 25.2 | High significant activity (P < 0.0001) |
| 7-Acetyloxycoumarin | 39.13 | High significant activity (P < 0.0001) |
| 4-Methyl-7-hydroxycoumarin | 17.39 | High significant activity (P < 0.0001) |
| 4-Methyl-7-methoxycoumarin | 48.91 | No significant activity |

TABLE 2-continued

In Vitro and In Vivo data of the coumarin compounds

| Compound | In Vitro (%) | In Vivo |
|---|---|---|
| 4-Methyl-7-acetyloxycoumarin | 23.91 | Significant activity (P < 0.01) |
| 4-Methyl-7,8-dihydroxycoumarin | 14.13 | No significant activity |
| 4-Methyl-7,8-dibenzyloxycoumarin | 24.1 | No significant activity |
| 4-Methyl-7,8-dimethoxycoumarin | 14.2 | No significant activity |
| 4-Methyl-7,8-diacetyloxycoumarin | 24.01 | No significant activity |

Advantages:
1. The compounds (±) Marmesin, Columbianetin, Dihydroxanthyletin and coumarin derivatives are useful as AChE inhibitors.
2. The percentage inhibition is high when compared to the earlier reported compounds.
3. All the above mentioned compounds are easily extractable from the natural source and can be synthesized efficiently in the laboratory.
4. Coumarin derivatives were efficiently synthesized in the laboratory.

We claim:

1. Method of treating Alzheimer's disease comprising administering a composition comprising an effective amount of 7-allyloxycoumarin, 7-Methoxycoumarin, 7-Acetyloxycoumarin, 4-Methyl-7-hydroxycoumarin, Columbianetin or pharmaceutically acceptable salts thereof optionally along with a pharmaceutically acceptable carrier, or diluents, wherein the effective dose of the composition is ranging between 50 to 100 mg/kg body weight in a subject in need thereof.

* * * * *